US006875428B2

(12) United States Patent
Mandeville, III et al.

(10) Patent No.: US 6,875,428 B2
(45) Date of Patent: Apr. 5, 2005

(54) LIPASE INHIBITING POLYMERS

(75) Inventors: W. Harry Mandeville, III, Lynnfield, MA (US); Molly Kate Boie, Allston, MA (US); Venkata R. Garigapati, Waltham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/359,458

(22) Filed: Feb. 5, 2003

(65) Prior Publication Data

US 2003/0185789 A1 Oct. 2, 2003

Related U.S. Application Data

(60) Division of application No. 09/714,541, filed on Nov. 16, 2000, now Pat. No. 6,558,657, which is a division of application No. 09/226,585, filed on Jan. 6, 1999, now Pat. No. 6,352,692, which is a continuation-in-part of application No. 09/166,510, filed on Oct. 5, 1998, now Pat. No. 6,267,952, which is a continuation-in-part of application No. 09/005,379, filed on Jan. 9, 1998, now abandoned.

(51) Int. Cl.$^7$ .............................................. A61K 31/74
(52) U.S. Cl. ............................... 424/78.08; 424/78.01; 514/909; 549/200; 549/208
(58) Field of Search ................................ 424/1.11, 1.65, 424/9.1, 78.08, 78.17, 78.37, 78.38, 78.01; 514/183, 449, 909; 549/200, 201, 208

(56) References Cited

U.S. PATENT DOCUMENTS

| | | | |
|---|---|---|---|
| 3,780,171 A | 12/1973 | Irmscher et al. | 424/79 |
| 3,923,972 A | 12/1975 | Fields et al. | 424/78 |
| 4,160,826 A | 7/1979 | Fischetti | 424/180 |
| 4,211,765 A | 7/1980 | Johnson et al. | 424/78 |
| 4,218,443 A | 8/1980 | Comai et al. | 424/181 |
| 4,265,879 A | 5/1981 | Fields et al. | 424/78 |
| 4,302,450 A | 11/1981 | Comai et al. | 424/181 |
| 4,432,968 A | 2/1984 | Page et al. | 424/78 |
| 4,959,179 A | 9/1990 | Aronson et al. | 252/135 |
| 5,063,210 A | 11/1991 | Lange, III et al. | 514/54 |
| 5,089,163 A | 2/1992 | Aronson et al. | 252/135 |
| 5,137,716 A | 8/1992 | Weisenfeld | 424/78.01 |
| 5,200,183 A | 4/1993 | Tang et al. | 424/94.6 |
| 5,286,481 A | 2/1994 | Weisenfeld | 424/78.01 |
| 5,308,766 A | 5/1994 | Dennis et al. | 435/184 |
| 5,376,674 A | 12/1994 | Derungs et al. | 514/422 |
| 5,401,498 A | 3/1995 | Kesseler et al. | 424/78.1 |
| 5,427,777 A | 6/1995 | St. Pierre et al. | 424/78.01 |
| 5,427,919 A | 6/1995 | Dennis et al. | 435/18 |
| 5,453,262 A | 9/1995 | Kanauchi et al. | 424/464 |
| 5,453,429 A | 9/1995 | Bliem et al. | 514/288 |
| 5,474,993 A | 12/1995 | Rubin et al. | 514/192 |
| 5,484,777 A | 1/1996 | Lange, III et al. | 514/54 |
| 5,567,597 A | 10/1996 | Dennis et al. | 435/18 |
| 5,569,452 A | 10/1996 | Amidon et al. | 424/78.1 |
| 5,597,810 A | 1/1997 | Hoffman et al. | 514/54 |
| 5,607,669 A | 3/1997 | Mandeville, III et al. | 424/78.12 |
| 5,618,530 A | 4/1997 | Mandeville, III et al. | 424/78.12 |
| 5,624,963 A | 4/1997 | Mandeville, III et al. | 514/789 |
| 5,629,338 A | 5/1997 | Okuda et al. | 514/451 |
| 5,665,348 A | 9/1997 | Okayama et al. | 424/78.35 |
| 5,674,482 A | 10/1997 | Regan et al. | 424/78.37 |
| 5,679,717 A | 10/1997 | Mandeville, III et al. | 514/742 |
| 5,693,675 A | 12/1997 | Mandeville, III et al. | 514/742 |
| 5,703,188 A | 12/1997 | Mandeville, III et al. | 526/290 |
| 5,750,524 A | 5/1998 | Mera et al. | 514/247 |
| 6,267,952 B1 | 7/2001 | Mandeville, III et al. | 424/78.08 |
| 6,352,692 B1 | 3/2002 | Mandeville, III et al. | 424/78.08 |

FOREIGN PATENT DOCUMENTS

| | | |
|---|---|---|
| EP | 0 050 347 A2 | 4/1982 |
| EP | 0 381 262 | 8/1990 |
| WO | WO 92/05788 | 4/1992 |

OTHER PUBLICATIONS

Gargouri, Y., et al., "Ajoene prevents fat digestion by human gastric lipase in vitro," *Biochimica et Biophysica Acta.* 1006:137–139 (1989).

Gargouri, Y., et al., "Covalent inhibition of digestive lipases: an in vitro study," *Biochimica et Biophysica Acta.* 1344:6–37 (1997).

Karamac, M. and Amarowicz, R., "Inhibition of Pancreatic Lipase by Phenolic Acids, Examination in vitro," *Verlag der Zeitschrift für Naturforschung*:903–905 (1996).

Marguet, F., et al., "Digestive lipases: inactivation by phosphonates," *Biochimica et Biophysica Acta.* 1210:157–166 (1994).

Mannesse, M.L.M., et al., "Phosphonate analogues of Triacylglycerols are potent inhibitors of lipase," *Biochimica et Biophysica Acta.* 1259:56–64 (1995).

Martichonok, V. and Jones, J.B., "(Z)–Heptadec–8–enylboronic acid: a potential lipase inhibitor," *J. Chem. Soc. Perkin Trans. I*:2927–2929 (1995).

Vainio, P., et al., "Inhibition of Lipoprotein Lipase by Benzene Boronic Acid Effect of Apolipoprotein C–II," *Biochimica et Biophysica Acta.* 711:386–390 (1982).

Bagree, A., et al., "Modification of ε– Amino Group of Lysine in Proteins by Acylation with Pyromellitic Dianhydride and o–Sulphobenzoic Anhydride," *FEBS Letters* 120(2):275–277 (1980).

(Continued)

Primary Examiner—Dameron L. Jones
(74) Attorney, Agent, or Firm—Ropes & Gray, LLP

(57) ABSTRACT

The invention features a method for treating obesity in a patient by administering to the patient a polymer that has been substituted with one or more groups that inhibit lipases, which are enzymes responsible for the hydrolysis of fat. The invention further relates to the polymers employed in the methods described herein as well as novel intermediates and methods for preparing the polymers.

9 Claims, No Drawings

OTHER PUBLICATIONS

Stadler, P., et al., "Inhibition of microbial lipases with stereoisomeric triradylglycerol analog phosphonates," *Biochimica et Biophysica Acta*. 1304:229–244 (1996).

Kawaguchi, K., et al., "Hesperidin as an Inhibitor of Lipases from Procine Pancreas and *Pseudomonas*," *Biosci. Biotech. Biochem.* 61(1):102–104 (1997).

Bochenek, W.J. and Rodgers, J.B., "Effect of Polyol Detergents on Cholesterol and Triglyceride Absorption," *Biochimica et Biophysica Acta* 489:503–506 (1977).

Comai, K. and Sullivan, A.C., "Antiobesity activity of pluronic L–101," *International Journal of Obesity* 4:33–42 (1980).

Han, L–K, et al., "Reduction in fat storage during chitin–chitosan treatment in mice fed a high–fat diet," *International Journal of Obesity* 23:174–179 (1999).

Moreau, Hervé, et al., "Inactivation of Gastric and Pancreatic Lipases by Diethyl *p*–Nitrophenyl Phosphate," *Biochemistry* 30:1037–1041 (1991).

Kataoka K. and Miyazaki H., "Sensitive Glucose–Induced Change of the Lower Critical Solution Temperature of Poly[*N,N*–dimethylacrylamide–*co*–3–(acrylamido) phenylboronic Acid] in Physiological Saline," *Macromolecules*, 27(4):1061–1062 (1994).

Wulff G. and Heinz–Günter P., "Influence of the Structure of the Binding Sites on the Selectivity for Racemic Resolution," *Makromol. Chem. 188*:741–745 (1987).

De B., et al., "An Unequivocal Approach to Ascertain Asymmetric Induction in the Polymer Main Chain during Enantioselective Copolymerization of 1,2–Disubstituted Olefins," *Macromolecules*, 29(1):468–470 (1996).

Bisse E. and Wieland H., "Coupling of *m*–aminophenylboronic Acid to *s*–triazine–activated Sephacryl: Use in the Affinity Chromatography of Glycated Hemoglobins," *Journal of Chromatography*, 575:223–228 (1992).

Hisamitsu, I., et al., "Glucose–Responsive Gel From Phenylborate Polymer and Poly(Vinyl Alcohol): Prompt Response at Physiological pH Through the Interaction of borate with Amino Group in the Gel," *Pharmaceutical Research,* 14(3):289–293.

Wulff, G., "Selective Binding to Polymer Via Covalent Bonds. The Construction of Chiral Cavities as Specific Receptor Sites," *Pure & Appl. Chem.,* 54(11):2093–2102 (1982).

Shiino D., et al., "Amine Effect on Phyenylboronic Acid Complex with Glucose Under Physiological pH in Aqueous solution," *Biomater. Sci. Polymer*, 2(8):697–705 (1996).

Miyazaki, H., et al., "Boronate–Containing Polymer as Novel Mitogen for Lymphocytes," *Biochemical and Biophysical Research Communications*, 195(2):829–836 (1993).

LIPASE INHIBITING POLYMERS

RELATED APPLICATION

This application is a Divisional of U.S. application Ser. No. 09/714,541, filed Nov. 16, 2000, now U.S. Pat. No. 6,558,657, which is a Divisional of U.S. Application Ser. No. 09/226,585, filed Jan. 6, 1999, now U.S. Pat. No. 6,352,692, which is a Continuation-in-Part of U.S. application Ser. No. 09/166,510 filed Oct. 5, 1998, now U.S. Pat. No. 6,267,952, which is a Continuation-in-Part of U.S. application Ser. No. 09/005,379 filed on Jan. 9, 1998, now abandoned, the entire teachings of which are incorporated herein by reference.

BACKGROUND OF THE INVENTION

Human obesity is a recognized health problem with approximately ninety-seven million people considered clinically overweight in the United States. The accumulation or maintenance of body fat bears a direct relationship to caloric intake. Therefore, one of the most common methods for weight control to combat obesity is the use of relatively low-fat diets, that is, diets containing less fat than a "normal diet" or that amount usually consumed by the patient.

The presence of fats in a great many food sources greatly limits the food sources which can be used in a low fat diet. Additionally, fats contribute to the flavor, appearance and physical characteristics of many foodstuffs. As such, the acceptability of low-fat diets and the maintenance of such diets are difficult.

Various chemical approaches have been proposed for controlling obesity. Anorectic agents such as dextroamphetamine, the combination of the non-amphetamine drugs phentermine and fenfluramine (Phen-Fen), and dexfenfluramine (Redux) alone, are associated with serious side effects. Indigestible materials such as olestra (OLEAN®), mineral oil or neopentyl esters (see U.S. Pat. No. 2,962,419) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk, as in U.S. Pat. No. 2,923,662. Surgical techniques such as temporary ileal bypass surgery, are employed in extreme cases.

However, methods for treating obesity, such as those described above have serious shortcomings with controlled diet remaining the most prevalent technique for controlling obesity. As such, new methods for treating obesity are needed.

SUMMARY OF THE INVENTION

The invention features a method for treating obesity in a patient by administering to the patient a polymer that has been substituted with or comprises one or more groups which can inhibit a lipase. Lipases are key enzymes in the digestive system which break down tri- and diglycerides, which are too large to be absorbed by the small intestine into fatty acids which can be absorbed. Therefore, inhibition of lipases results in a reduction in the absorption of fat. In one embodiment, the lipase inhibiting group can be a "suicide substrate" which inhibits the activity of the lipase by forming a covalent bond with the enzyme either at the active site or elsewhere. In another embodiment, the lipase inhibiting group is an isosteric inhibitor of the enzyme. The invention further relates to the polymers employed in the methods described herein as well as novel intermediates and methods for preparing the polymers.

DETAILED DESCRIPTION OF THE INVENTION

The invention features a method for treating obesity in a patient by administering to the patient a polymer comprising one or more groups which can inhibit a lipase. Since lipases are responsible for the hydrolysis of fat, a consequence of their inhibition is a reduction in fat hydrolysis and absorption. The invention further relates to the polymers employed in the methods described herein as well as novel intermediates and methods for preparing the polymers.

In one aspect of the invention, the lipase inhibiting group inactivates a lipase such as gastric, pancreatic and lingual lipases. Inactivation can result by forming a covalent bond such that the enzyme is inactive. The covalent bond can be formed with an amino acid residue at or near the active site of the enzyme, or at a residue which is distant from the active site provided that the formation of the covalent bond results in inhibition of the enzyme activity. Lipases contain a catalytic triad which is responsible for the hydrolysis of lipids into fatty acids. The catalytic triad consists of a serine, aspartate and histidine amino acid residues. This triad is also responsible for the hydrolysis of amide bonds in serine proteases, and it is expected that compounds that are serine protease inhibitors will also inhibit lipases. Therefore, serine protease inhibitors that can be covalently linked to a polymer are preferred lipase inhibiting groups. For example, a covalent bond can be formed between the lipase inhibiting group and a hydroxyl at or the catalytic site of the enzyme. For instance, a covalent bond can be formed with serine. Inactivation can also result from a lipase inhibiting group forming a covalent bond with an amino acid, for example cysteine, which is at some distance from the active site. In addition, non-covalent interaction between the lipase inhibiting group and the enzyme can also result in inactivation of the enzyme. For example, the lipase inhibiting group can be an isostere of a fatty acid, which can interact non-covalently with the catalytic site of the lipase. In addition, the lipase inhibiting group can compete for lipase hydrolysis with natural triglycerides.

In one aspect of the invention, a lipase inhibiting group can be represented by formula I:

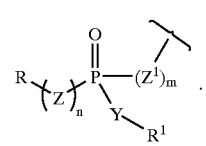

I wherein,

R is a hydrogen, hydrophobic moiety, —NR²R³, —CO₂H, —OCOR², —NHCOR², a substituted or unsubstituted aliphatic group or a substituted or unsubstituted aromatic group;

$R^1$ is an activating group;

Y is oxygen, sulfur, —NR²— or is absent;

Z and $Z^1$ are, independently, an oxygen, alkylene, sulfur, —SO₃—, —CO₂—, —NR²—, —CONR²—, —PO₄H— or a spacer group;

$R^2$ and $R^3$ are, independently, a hydrogen, a substituted or unsubstituted aliphatic group, or a substituted or unsubstituted aromatic group;

m is 0 or 1; and
n is 0 or 1.

In one embodiment, the lipase inhibiting group of formula I can be represented by the following structures:

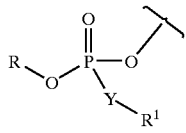

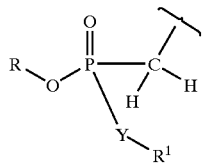 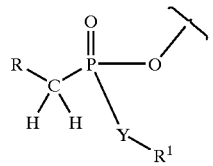

wherein R, R$^1$ and Y are defined as above.

In another embodiment, the lipase inhibiting group of structural formula I can be represented by the following structures:

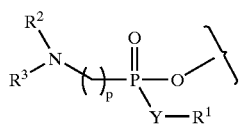 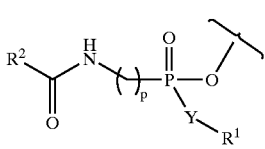

wherein R, R$^1$, R$^2$, R$^3$ and Y are defined as above, and p is an integer (e.g. an integer between zero and about 30, preferably between about 2 and about 10).

In another embodiment, the lipase inhibitor of formula I is a mixed anhydride. Mixed anhydrides include, but are not limited to, phosphoric-carboxylic, phosphoric-sulfonic and pyrophosphate mixed anhydride lipase inhibiting groups which can be represented by the following structures, respectively:

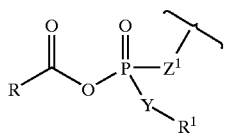 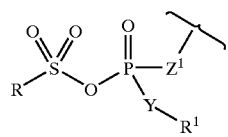

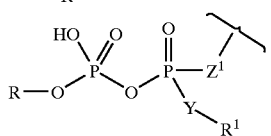

wherein R, R$^1$, Y and Z$^1$ are defined as above.

In another aspect, a lipase inhibiting group of the invention can be an anhydride. In one embodiment, the anhydride is a cyclic anhydride represented by formula II:

II

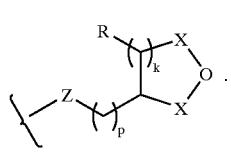

wherein R, Z and p are defined as above, X is —PO$_2$—, —SO$_2$— or —CO—, and k is an integer from 1 to about 10, preferably from 1–4.

In another embodiment, the anhydride lipase inhibiting groups can be a cyclic anhydride which is part of a fused ring system. Anhydrides of this type can be represented by formula III:

III

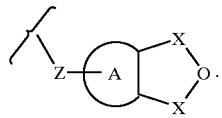

wherein X and Z are defined as above, and ring A is an optionally substituted cyclic aliphatic group or aromatic group, or combinations thereof, which can include one or more heteroatoms in the ring. In a particular embodiment, the cyclic anhydride is a benzenesulfonic anhydride represented by the following structure:

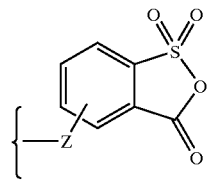

wherein Z is defined as above and the benzene ring can be further substituted.

In another aspect, the lipase inhibiting group is an α-halogenated carbonyl which can be represented by formula IV:

IV

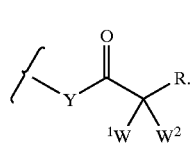

wherein R and Y are defined as above, and W$^1$ and W$^2$ are each independently hydrogen or halogen, for example, —F, —Cl, —Br, and —I, wherein at least one of W$^1$ and W$^2$ is a halogen.

In yet another aspect, a cyclic compound having an endocyclic group that is susceptible to nucleophilic attack can be a lipase inhibiting group. Lactones and epoxides are examples of this type of lipase inhibiting group and can be represented by formulas V and VI, respectively:

V

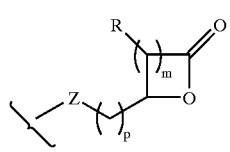

VI

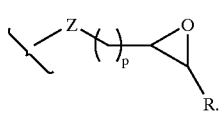

wherein R, Z, m and p are defined as above.

In a further aspect, the lipase inhibiting group can be a sulfonate or disulfide group represented by formulas VII and VIII, respectively:

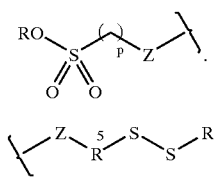

VII

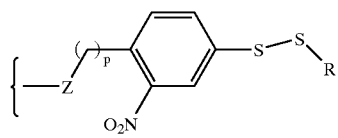

VIII wherein R, Z and p are defined as above, and $R^5$ is absent or a hydrophobic moiety, a substituted or unsubstituted aliphatic group or a substituted or unsubstituted aromatic group.

In a particular embodiment, the disulfide lipase inhibiting group can be represent by the following formula:

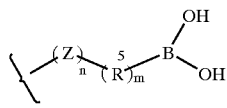

wherein R, Z and p are defined as above.

In a further aspect of the invention, a lipase inhibiting group can be a boronic acid which can be linked to a polymer by a hydrophobic group or to the polymer directly when the polymer is hydrophobic. Boronic acid lipase inhibiting groups can be represented by the following structure:

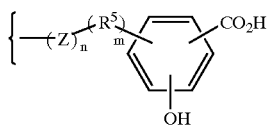

wherein $R^5$, Z, n and m are defined as above.

In an additional aspect, an isosteric lipase inhibiting group can be a phenolic acid linked to the polymer. Phenolic acid lipase inhibiting groups can be represented by the following structure:

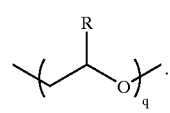

wherein Z, $R^5$, n and m are defined as above and —$CO_2H$ and —OH are ortho or para with respect to each other.

A variety of polymers can be employed in the invention described herein. The polymers can be aliphatic, alicyclic or aromatic or synthetic or naturally occurring. However, aliphatic and alicyclic synthetic polymers are preferred. Furthermore, the polymer can be hydrophobic, hydrophilic or copolymers of hydrophobic and/or hydrophilic monomers. The polymer can be non-ionic (e.g., neutral), anionic or cationic, in whole or in part. Furthermore, the polymers can be manufactured from olefinic or ethylenic monomers (such as vinylalcohol) or condensation polymers.

For example, the polymers can be a polyvinylalcohol, polyvinylamine, poly-N-alkylvinylamine, polyallylamine, poly-N-alkylallylamine, polyalkylenimine, polyethylene, polypropylene, polyether, polyethylene oxide, polyamide, polyacrylic acid, polyalkylacrylate, polyacrylamide, polymethacrylic acid, polyalkylmethacrylate, polymethacrylamide, poly-N-alkylacrylamide, poly-N-alkylmethacrylamide, polystyrene, vinylnaphthalene, ethylvinylbenzene, aminostyrene, vinylbiphenyl, vinylanisole, vinylimidazolyl, vinylpyridinyl, dimethylaminomethylstyrene, trimethylammoniumethylmethacrylate, trimethylammoniumethylacrylate, carbohydrate, protein and substituted derivatives of the above (e.g., fluorinated monomers thereof) and copolymers thereof.

Preferred polymers include polyethers, such as polyalkylene glycols. Polyethers can be represented by the formula IX:

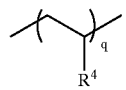

IX wherein R is defined as above and q is an integer.

For example, the polymer can be polypropylene glycol or polyethylene glycol or copolymers thereof. The polymers can be random or block copolymers. Also, the polymers can be hydrophobic, hydrophilic, or a combination thereof (as in random or block polymers).

A particularly preferred polymer is a block copolymer characterized by hydrophobic and hydrophilic polymeric regions. In such an embodiment, the "core polymer can be hydrophobic with one or both ends capped with a hydrophilic polymer or vice versa. An example of such a polymer is a polyethyleneglycol-polypropyleneglycol-polethyleneglycol copolymer, as is sold under the tradename PLURONIC® (BASF Wyandotte Corp.). BRIJ® and IGEPAL® (Aldrich, Milwaukee, Wis.) are examples of polymers having a polyethylene glycol core capped withe a hydrophobic end group. BRIJ® polymers are polyethylene glycols having one end capped with alkoxy group, while the hydroxy group at the other end of the polymer chain is free. IGEPAL® polymers are polyethylene glycols having one end capped with 4-nonylphenoxy group, while the hydroxy group at the other end of the polymer chain is free.

Another class of polymers includes aliphatic polymers such as, polyvinylalcohol, polyallylamine, polyvinylamine and polyethylenimine. These polymers can be further characterized by one or more substituents, such as substituted or unsubstituted, saturated or unsaturated alkyl and substituted or unsubstituted aryl. Suitable substituents include anionic, cationic or neutral groups, such as alkoxy, aryl, aryloxy, aralkyl, halogen, amine, and ammonium groups, for example. The polymer can desirably possess one or more reactive functional groups which can, directly or indirectly, react with an intermediate possessing the lipase inhibiting groups.

In one embodiment, the polymers have the following repeat unit:

wherein, q is an integer; and $R^4$ is —OH, —$NH_2$, —$CH_2NH_2$, —SH, or a group represented by the following formula:

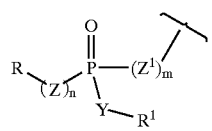

wherein R, $R^1$, Y, Z, $Z^1$, m and n are defined as above.

Additionally, the polymer can be a carbohydrate, such as chitosan, cellulose, hemicellulose or starch or derivatives thereof.

The polymer can be linear or crosslinked. Crosslinking can be performed by reacting the copolymer with one or more crosslinking agents having two or more functional groups, such as electrophilic groups, which react with an alcohol of the polymer to form a covalent bond. Crosslinking in this case can occur, for example, via nucleophilic attack of the polymer hydroxy groups on the electrophilic groups. This results in the formation of a bridging unit which links two or more alcoholic oxygens from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes.

The polymer composition can also be crosslinked by including a multifunctional co-monomer as the crosslinking agent in the reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, diallylacrylamides, and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The molecular weight of the polymer is not critical. It is desirable that the polymer be large enough to be substantially or completely non-absorbed in the GI tract. For example, the molecular weight can be more than 900 Daltons.

The digestion and absorption of lipids is a complex process in which water insoluble lipids are emulsified to form an oil in water emulsion with an oil droplet diameter of approximately 0.5 mm. This emulsified oil phase has a net negative charge due to the presence of fatty acids and bile salts, which are the major emulsifying agents. Lipases that are present in the aqueous phase hydrolyze the emulsified lipids at the emulsion surface. Most lipases contain an active site that is buried by a surface loop of amino acids that sit directly on top of the active site when the lipase is in an aqueous solution. However, when the lipase comes in contact with bile salts at the lipid/water interface of a lipid emulsion, the lipase undergoes a conformational change that shifts the surface loop to one side and exposes the active site. This conformational change allows the lipase to catalyze hydrolysis of lipids at the lipid/water interface of the emulsion. Polymers that disrupt the surface of the emulsion or alter its chemical nature are expected to inhibit lipase activity. Therefore, it may increase the effectiveness of polymers that have lipase inhibiting groups to administer them with one or more polymers that alter the emulsion surface. Alternatively, lipase inhibiting groups can be attached directly to such a polymer.

Several types of fat-binding polymers have been effective in disrupting the surface of the lipid emulsion or altering its chemical nature. For example, polymers that have positively charged emulsifiers are able to form stable polycation lipid emulsions. The lipids in such an emulsion are not substrates for gastrointestinal lipases because the surface of the emulsion has a net positive charge instead of the usual net negative charge. Another type of fat-binding polymer destabilizes the emulsion causing the oil droplets of the emulsion to coalesce. This decreases the emulsion surface area where lipases are active, and therefore, reduces lipid hydrolysis. Fat-binding polymer are further defined in copending application Ser. No. 09/004,963, filed on Jan. 9, 1998, and application Ser. No. 09/166,453, filed on Oct. 5, 1998, the contents of which are incorporated herein by reference.

The substituted polymers described herein can be manufactured according to methods generally known in the art. For example, a lipase inhibiting intermediate characterized by a reactive moiety can be contacted with a polymer characterized by a functional group which reacts with said reactive moiety. See March, J., Advanced Organic Chemistry, $3^{rd}$ edition, John Wiley and Sons, Inc.; New York, (1985).

A "hydrophobic moiety," as the term is used herein, is a moiety which, as a separate entity, is more soluble in octanol than water. For example, the octyl group ($C_8H_{17}$) is hydrophobic because its "parent" alkane, octane, has greater solubility in octanol than in water. The hydrophobic moieties can be a saturated or unsaturated, substituted or unsubstituted hydrocarbon group. Such groups include substituted and unsubstituted, normal, branched or cyclic aliphatic groups having at least four carbon atoms, substituted or unsubstituted arylalkyl or heteroarylalkyl groups and substituted or unsubstituted aryl or heteroaryl groups. Preferably, the hydrophobic moiety includes an aliphatic group of between about six and thirty carbons. Specific examples of suitable hydrophobic moieties include the following alkyl groups: butyl, pentyl, hexyl, heptyl, octyl, nonyl, decyl, dodecyl, tetradecyl, hexadecyl, octadecyl, docosanyl, cholesteryl, farnesyl, aralkyl, phenyl, and naphthyl, and combinations thereof. Other examples of suitable hydrophobic moieties include haloalkyl groups of at least four carbons (e.g., 10-halodecyl), halodecyl), hydroxyalkyl groups of at least six carbons (e.g., 11-hydroxyundecyl), and aralkyl groups (e.g., benzyl). As used herein aliphatic groups include straight, chained, branched or cyclic $C_4$–$C_{30}$ hydrocarbons which are completely saturated or contain one or more units of unsaturation.

Aromatic groups suitable for use in the invention include, but are not limited to, aromatic rings, for example, phenyl and substituted phenyl, heteroaromatic rings, for example, pyridinyl, furanyl and thiophenyl, and fused polycyclic aromatic ring systems in which a carbocyclic aromatic ring or heteroaryl ring is fused to one or more other carbocyclic or heteroaryl rings. Examples of fused polycyclic aromatic ring systems include substituted or unsubstituted phenanthryl, anthracyl, naphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridintyl.

A "substituted aliphatic or aromatic group" can have one or more substituents, e.g., an aryl group (including a carbocyclic aryl group or a heteroaryl group), a substituted aryl group, —O-(aliphatic group or aryl group), —O-(substituted aliphatic group or substituted aryl group), acyl, —CHO, —CO-(aliphatic or substituted aliphatic group), —CO-(aryl or substituted aryl), —COO-(aliphatic or substituted aliphatic group), —COO-(aryl or substituted aryl group), —NH-(acyl), —O-(acyl), benzyl, substituted benzyl, halogenated lower alkyl (e.g. trifluoromethyl and trichloromethyl), fluoro, chloro, bromo, iodo, cyano, nitro, —SH, —S-(aliphatic or substituted aliphatic group), —S-(aryl or substituted aryl), —S-(acyl) and the like.

An "activating group" is a group that renders a functional group or moiety reactive. Generally, electron withdrawing groups are "activating groups." $R^1$ or Y—$R^1$, of the above formulae, is preferably a good leaving group or an electron withdrawing group. Examples of good leaving groups are phosphate, p-nitrophenol, o,p-dinitrophenol, N-hydroxysuccinimide, imidazole, ascorbic acid, pyridoxine, trimethylacetate, adamantanecarbonylate, p-chlorophenol, o,p-dichlorophenol, methanesulfonylate, mesitylsulfonylate and triisopropylbenzenesulfonylate. A preferred leaving group is N-hydroxysuccinimide.

A spacer group can be a group that has one to about thirty atoms and is covalently bonded to the lipase inhibitor, to the polymer, or to the hydrophobic moiety. Generally, the spacer group can be covalently bonded to the lipase inhibitor, polymer or hydrophobic moiety through a functional group. Examples of functional groups are oxygen, alkylene, sulfur, —$SO_2$—, —$CO_2$—, —$NR^2$—, or —$CONR^2$—. A spacer group can be hydrophilic or hydrophobic. Examples of spacer groups include amino acids, polypeptides, carbohydrates, and optionally substituted alkylene or aromatic groups. Spacer groups can be manufactured from, for example, epichlorohydrin, dihaloalkane, haloalkyl esters, polyethylene glycol, polypropylene glycol and other cross-linking or difunctional compounds. Bromoalkylacetate is a preferred spacer group.

The amount of a polymer administered to a subject will depend on the type and severity of the disease and on the characteristics of the subject, such as general health, age, body weight and tolerance to drugs. It will also depend on the degree of obesity and obesity related complications. The skilled artisan will be able to determine appropriate dosages depending on these and other factors. Typically, in human subjects, an effective amount of the polymer can range from about 10 mg per day to about 50 mg per day for an adult. Preferably, the dosage ranges from about 10 mg per day to about 20 mg per day.

The polymer can be administered by any suitable route, including, for example, orally in capsules, suspensions or tablets. Oral administration by mixing with food is a preferred mode of administration.

The polymer can be administered to the individual in conjunction with an acceptable pharmaceutical carrier as part of a pharmaceutical composition. Formulation of a polymer to be administered will vary according to the route of administration selected (e.g., solution, emulsion, capsule). Suitable pharmaceutical carriers may contain inert ingredients which do not interact with the lipase inhibiting groups of the polymer. Standard pharmaceutical formulation techniques can be employed, such as those described in Remington's Pharmaceutical Sciences, Mack Publishing Company, Easton, Pa. Methods for encapsulating compositions (such as in a coating of hard gelatin or cyclodextran) are known in the art (Baker, et al., "Controlled Release of Biological Active Agents", John Wiley and Sons, 1986).

EXPERIMENTAL

Synthesis of Polymers

EXAMPLE 1

Preparation of polyethylene glycol having an n-pentyl hydroprobic moiety and p-nitrophenyl phosphate lipase inhibiting groups:

A mixture of n-pentanol (19.5 mmol. 1.72 g) and N-methyl imidazole (19.5 mmol, 1.6 g) in anhydrous methylene chloride (40 mL) was added slowly over 20 minutes under anhydrous conditions to a solution of p-nitrophenyl phosphorodichloridate (5.0 g, 19.5 mmol) in anhydrous methylene chloride (100 mL). The reaction flask was cooled in a water bath during the addition. After the completion of the addition, the water bath was removed, and the reaction mixture was stirred for 2 hours at room temperature. A mixture of polyethyleneglycol (MW=8,000; 10 mmol, 80 g), and N-methyl imidazole (19.5 mmol, 1.6 g) in anhydrous methylene chloride (150 mL) was added to the reaction flask under anhydrous conditions. The mixture was stirred for 25 hours at room temperature. The solvent was removed under vacuum, the residue was purified according to method A, and the polymer was obtained as white powder (70 g).

Purification Procedures

Method A:

The residue was dissolved in de-ionized water (100 mL). The solution was dialyzed for 24 hours using Spectra/Por Membrane MWCO: 3,500. The dialyzed solution was lyophilized, and the polymer was obtained as white powder.

Method B:

The residue was poured into 0.5 L of diethyl ether and stirred at room temperature for 1 hour. The solvent was decanted and replaced with fresh diethyl ether (0.25 L). The mixture was stirred for 1 hour. The solvent was removed, and the polymer was dried at room temperature under vacuum.

Method C:

The reaction mixture was washed with 10% aqueous sodium sulfate solution (3×100 mL). The organic phase was dried over magnesium sulfate. The solvent was removed, and the polymer was dried at room temperature.

Using the above procedures, the following compounds were synthesized and are tabulated in the following table.

TABLE 1

Polyethylene glycols (PEG) having p-nitrophenyl phosphate lipase inhibiting groups with a variety of hydroprobic moieties.

| EXAMPLE | PEG MW | HYDROPHOBIC MOIETY (R) | METHOD OF PURIFICATION | PHYSICAL STATE |
|---|---|---|---|---|
| 1 | 8,400 | n-pentyl | Method A | powder |
| 2 | 3,400 | n-decyl | Method B | powder |
| 3 | 3,400 | n-dodecyl | Method B | powder |
| 4 | 3,400 | n-octadecyl | Method B | powder |
| 5 | 1,000 | n-decyl | Method B | semi solid |
| 6 | 1,000 | n-dodecyl | Method B | semi solid |
| 7 | 1,000 | n-tetradecyl | Method B | semi solid |
| 8 | 1,000 | n-hexadecyl | Method B | semi solid |
| 9 | 1,000 | n-octadecyl | Method B | semi solid |
| 10 | 1,000 | n-pentyl | Method C | semi solid |
| 11 | 1,000 | n-hexyl | Method C | semi solid |

TABLE 1-continued

Polyethylene glycols (PEG) having p-nitrophenyl phosphate lipase inhibiting groups with a variety of hydroprobic moieties.

| EXAMPLE | PEG MW | HYDROPHOBIC MOIETY (R) | METHOD OF PURIFICATION | PHYSICAL STATE |
|---|---|---|---|---|
| 12 | 1,000 | n-octyl | Method C | semi solid |
| 13 | 1,000 | n-docosyl | Method C | powder |
| 14 | 1,000 | cholesteryl | Method C | powder |
| 15 | 3,400 | n-pentyl | Method B | solid |
| 16 | 1,500 | n-pentyl | Method B | solid |
| 17 | 1,500 | n-decyl | Method B | solid |
| 18 | 1,500 | n-dodecyl | Method B | solid |
| 19 | 1,500 | n-hexadecyl | Method C | solid |
| 20 | 1,500 | n-octadecyl | Method C | solid |
| 21 | 1,500 | n-docosyl | Method B | solid |
| 22 | 1,500 | rac-farnesyl | Method B | brown, solid |
| 23 | 1,500 | n-cholesteryl | Method C | solid |
| 24 | 1,500 | 5-phenyl-1-pentyl | Method C | solid |
| 25 | 1,500 | n-octyl | Method C | solid |
| 26 | 1,500 | n-hexyl | Method C | solid |
| 27 | 3,400 | n-octyl | Method C | solid |
| 28 | 8,400 | n-octyl | Method C | solid |

EXAMPLE 29

Preparation of a PLURONIC® polymer having a n-tetradecyl hydrophobic moiety and p-nitrophenyl phosphate lipase inhibiting groups:

A mixture of n-tetradecanol (15 g, 70 mmol) and N-methyl imidazole (5.6 mL, 70 mmol) in anhydrous methylene chloride (75 mL) was added slowly over 20 minutes under anhydrous condition to a solution of p-nitrophenyl phosphorodichloridate (17.92 g, 70 mmol) in anhydrous methylene chloride (50 mL). The reaction flask was cooled in a water bath during the addition. After the completion of the addition, the water bath was removed, and the reaction mixture was stirred for 2 hours at room temperature. A mixture of PLURONIC® (MW=1,100; 39 g, 35 mmol) and N-methyl imidazole (5.6 mL. 70 mmol) in anhydrous methylene chloride (150 mL) was added to the reaction flask under anhydrous conditions. The mixture was stirred for 24 hours at room temperature. The reaction mixture was extracted with cold saturated NaCl solution (3×150 mL), the organic layer was dried over anhydrous sodium sulfate. The sodium sulfate was removed by filtration, and the filtrate was collected. The solvent was removed from the filtrate under reduced pressure to give 65 g of pale yellow colored viscous liquid. The material was dried under vacuum for one week at room temperature. This was used directly for the in vitro and in vivo assay.

The following Examples were prepared using the above procedure.

TABLE 2

PLURONIC® Polymers (PLU) having p-nitrophenyl phosphate lipase inhibiting groups with a variety of hydrophobic moieties.

| EXAMPLE | PLU MW | WT. % ETHYLENE GLYCOL | HYDROPHOBIC MOIETY (R) | PHYSICAL STATE |
|---|---|---|---|---|
| 29 | 1,100 | 10 wt % | n-tetradecyl | liquid |
| 30 | 1,100 | 10 wt % | n-dodecyl | liquid |
| 31 | 1,100 | 10 wt % | n-decyl | liquid |
| 32 | 1,100 | 10 wt % | n-oetyl | liquid |
| 33 | 1,900 | 50 wt % | n-hexyl | liquid |
| 34 | 1,900 | 50 wt % | n-octyl | liquid |
| 35 | 1,900 | 50 wt % | n-decyl | liquid |
| 36 | 1,900 | 50 wt % | n-dodecyl | liquid |
| 37 | 1,900 | 50 wt % | n-tetradecyl | semi solid |
| 38 | 1,900 | 50 wt % | n-hexadecyl | semi solid |
| 39 | 8,400 | 80 wt % | n-pentyl | powder |
| 40 | 8,400 | 80 wt % | n-hexyl | powder |
| 41 | 2,900 | 40 wt % | n-octadecyl | semi solid |
| 42 | 2,900 | 40 wt % | n-hexadecyl | semi solid |
| 43 | 2,900 | 40 wt % | n-tetradecyl | liquid |
| 44 | 2,900 | 40 wt % | n-dodecyl | liquid |
| 45 | 4,400 | 40 wt % | n-octadecyl | semi solid |
| 46 | 4,400 | 40 wt % | n-hexadecyl | semi solid |
| 47 | 4,400 | 40 wt % | n-tetradecyl | liquid |
| 48 | 4,400 | 40 wt % | n-dodecyl | liquid |

EXAMPLE 51

Preparation of a polypropylene glycol having a n-hexadecyl hydrophobic moiety and p-nitrophenyl phosphate lipase inhibiting group:

A mixture of n-hexadecanol (28.41 g, 117 mmol) and N-methyl imidazole (9.34 mL, 117 mmol) in anhydrous methylene chloride (75 mL) was added slowly over 20 minutes under anhydrous condition to a solution of p-nitrophenyl phosphorodichloridate (30 g, 117 mmol) in anhydrous methylene chloride (60 mL). The reaction flask was cooled in a water bath during the addition. After the completion of the addition, the water bath was removed and the reaction mixture was stirred for 2 hours at room temperature. A mixture of polypropylene glycol (MW=1000; 58.5 g, 58.5 mmol) and N-methyl imidazole (9.3 mL, 117 mmol) in anhydrous methylene chloride (150 mL) was added to the reaction flask under anhydrous conditions. The mixture was stirred for 24 hours at room temperature. The reaction mixture was extracted with cold saturated solution of $Na_2SO_4$ (3×150 mL). The organic layer was dried over anhydrous magnesium sulfate. The magnesium sulfate was removed by filtration, and the filtrate was collected. The solvent was removed from the filtrate under reduced pressure to give a product of 77 g. The material was dried under vacuum at room temperature for 4 days.

The following polypropylene glycol p-nitrophenyl phosphates were prepared using the above procedure.

TABLE 3

Polypropylene glycol (PPG) having p-nitrophenyl phosphate lipase inhibiting groups with a variety of hydrophobic moieties.

| EXAMPLE | PPG MW | HYDROPHOBIC MOIETY (R) | PHYSICAL STATE |
|---|---|---|---|
| 49 | 1,000 | n-pentyl | semi solid |
| 50 | 1,000 | n-octyl | semi solid |
| 51 | 1,000 | n-hexadecyl | semi solid |
| 52 | 1,000 | n-octadecyl | semi solid |
| 53 | 2,000 | n-pentyl | semi solid |
| 54 | 2,000 | n-octyl | semi solid |

TABLE 3-continued

Polypropylene glycol (PPG) having p-nitrophenyl phosphate lipase inhibiting groups with a variety of hydrophobic moieties.

| EXAMPLE | PPG MW | HYDROPHOBIC MOIETY (R) | PHYSICAL STATE |
|---|---|---|---|
| 55 | 2,000 | n-hexadecyl | semi solid |
| 56 | 2,000 | n-octadecyl | semi solid |

EXAMPLE 57

Preparation of a polyethylene glycol polymer having a p-nitrophenyl phosphonate lipase inhibiting group and having a pentyl hydrophobic moieties:

A. Preparation of O,O-dimethyl n-pentylphosphonate:

O,O-dimethyl phosphonate (220 g, 2 mol) was added dropwise to a suspension of NaH (48 g, 2 mol) in anhydrous THF (600 mL) under nitrogen. After 1 hour, 1-bromopentane (248 mL, 2 mol) in THF (400 mL) was added slowly, and the reaction mixture was refluxed for 12 hours. The solvent was removed under vacuum, diethyl ether (1 L) was added, and the salts were removed by filtration. The ether solution was washed with water (3×100 mL), the organic layer was dried over anhydrous sodium sulfate. The ether was removed under reduced pressure, and the crude product was purified by distillation under vacuum to give 171 g of O,O-dimethyl n-pentyl phosphonate.

B. Preparation of n-pentylphosphonic dichloride:

O,O-dimethyl n-pentyl phosphonate (158 g, 0.88 mol) and N,N-dimethyl formamide (700 mg) were dissolved in thionyl chloride (200 mL), and the resulted mixture was refluxed for 48 hours. The volatiles were removed under vacuum at room temperature, and the crude product was purified by distillation to give a colorless liquid (135 g).

C. Preparation of polyethylene glycol Having a p-nitrophenyl n-pentyl phosphonate lipase inhibiting groups:

To a solution of n-pentylphosphonic dichloride (2.65 g, 14 mmol) in 40 mL of anhydrous dichloromethane, was added bright orange colored sodium salt of p-nitrophenol (2.3 g, 14 mmol) under anhydrous condition. The bright orange color disappeared within 5-10 minutes. After 45 minutes, a mixture of polyethylene glycol (MW=8,400; 56 g, 7 mmol) and N-methylimidazole (1.5 mL, 20 mmol) was added at room temperature and stirred for 24 hours. The reaction mixture was washed with 2% $K_2CO_3$ solution (6×100 mL) followed by saturated NaCl solution (6×100 mL). The organic layer was dried over $Na_2SO_4$, the solvent was removed under vacuum to give a viscous liquid. The product was poured into 200 mL of diethyl ether and stirred for 10 minutes. The ether portion was decanted, and the procedure was repeated three more times. The product was obtained as a white powder which was dried under vacuum at room temperature for a week.

The following polyethylene glycol polymers having p-nitrophenyl phosphonate lipase inhibiting groups were prepared by this procedure.

TABLE 4

Polyethylene glycols having p-nitrophenyl phosphonate lipase inhibiting groups with a pentyl hydrophobic moiety.

| EXAMPLE | PEG | HYDROPHOBIC MOIETY (R) | PHYSICAL STATE |
|---|---|---|---|
| 57 | 8,400 | n-pentyl | powder |
| 58 | 3,400 | n-pentyl | powder |
| 59 | 1,500 | n-pentyl | semi solid |
| 60 | 1,000 | n-pentyl | semi solid |

EXAMPLE 61

Preparation of a PLURONIC® polymer having p-nitrophenyl phosphates lipase inhibiting group tethered by a n-pentyl-1,5-dioxy linker and having a n-hexadecyl hydrophobic moiety:

A 1 L, round-bottomed flask was charged with sodium hydride (4.0 g as a 60% dispersion of NaH in mineral oil, 0.1 mol) then washed with anhydrous heptane (3×25 mL). Anhydrous tetrahydrofuran (THF) (150 mL) was added, and the suspension was stirred at room temperature under nitrogen. A solution of PLURONIC® (MW=1900, 50 wt % polyethylene glycol, 50 wt % polypropylene glycol; 95 g, 0.05 mole) in anhydrous THF (200 mL) was added at room temperature. A solution of bromopentyl acetate (20.9 g, 0.1 mole) in anhydrous THF (50 mL) was added to the reaction mixture under anhydrous conditions. The reaction mixture was refluxed at 60° C. for 16 hours. The solvent was removed under vacuum, and the resulting slurry was suspended in dichloromethane (300 mL). The solids were removed by filtration, and the filtrate was washed with water (3×100 mL). The organic layer was dried over anhydrous sodium sulfate, and the solvent was removed to give a pale brown viscous liquid (110 g). This material was dissolved in methanol (500 mL) and treated with aqueous 4N NaOH (40 mL). After 4 hours, the reaction mixture was acidified with concentrated HCl, and the solvent was removed under vacuum. The viscous oil was dissolved in dichloromethane, which was washed with water (4×100 mL). The organic layer was dried over sodium sulfate, and the solvent was removed to give bis-5-hydroxypentoxy PLURONIC® as a pale brown viscous liquid (98 g).

In a separate flask, a mixture of n-hexadecanol (7.02 g, 29.0 mmol) and N-methyl imidazole (2.3 mL, 290 mmol) in anhydrous methylene chloride (40 mL) was added slowly over 20 minutes under anhydrous conditions to a solution of p-nitrophenyl phosphorodichloridate (7.41 g, 29.0 mmol) in anhydrous methylene chloride (100 mL). The reaction flask was cooled in a water bath during the addition. After the completion of the addition, the water bath was removed, and the reaction mixture was stirred for 2 hours at room temperature. A mixture of bis-5-hydroxypentoxy PLURONIC® (30 g, 14.48 mmol), and N-methyl imidazole (2.3 mL) in anhydrous methylene chloride (150 mL) was added to the reaction flask under anhydrous conditions. The mixture was stirred for 24 hours at room temperature, then washed with saturated NaCl solution (3×100 mL). The organic layer was collected and dried over sodium sulfate. The solvent was removed to give a viscous liquid. This was washed with boiling hexane (6×50 mL), and the product was dried under vacuum at room temperature overnight to yield a pale yellow viscous liquid (39 g).

The following Examples were prepared using the above procedure.

TABLE 5

PLURONIC ® polymers having p-nitrophenyl phosphate lipase inhibiting groups tethered by a variety of dialkoxys and having a variety of hydrophobic moieties.

| EXAMPLE | PLU MW | HYDROPHOBIC MOIETY (R) | DIALKOXY ($Z^1$) |
|---|---|---|---|
| 61 | 1900 | n-pentyl | n-pent-1,5-dioxy |
| 62 | 1900 | n-decyl | n-pent-1,5-dioxy |
| 63 | 1900 | n-hexadecyl | n-pent-1,5-dioxy |
| 64 | 1900 | n-pentyl | n-undecyl-1,10-dioxy |
| 65 | 1900 | n-decyl | n-undecyl-1,10-dioxy |
| 66 | 1900 | n-hexadecyl | n-undecyl-1,10-dioxy |

EXAMPLE 67

Preparation of a polyethylene glycol polymer having a p-nitrophenyl phosphates lipase inhibiting group tethered by a n-pentyl-1,5-dioxy linker and having a n-hexadecyl hydrophobic moiety:

A 1 L, round-bottomed flask was charged with sodium hydride (7.67 g as a 60% dispersion of NaH in mineral oil, 0.19 mol) and was washed with anhydrous heptane (3×25 mL). Anhydrous THF (200 mL) was added, and the suspension was stirred at room temperature under nitrogen. A solution of polyethylene glycol (MW=1,500; 150 g, 0.1 mol) in anhydrous THF (200 mL) was added at room temperature under anhydrous conditions. The mixture was stirred for 1 hour at room temperature, then a solution of bromopentyl acetate (41.82 g, 0.2 mol) in anhydrous THF (100 mL) was added to the reaction mixture. The reaction mixture was refluxed at 60° C. for 16 hours. The solvent was removed under vacuum, and the resulting slurry was suspended in dichloromethane (300 mL). The solids were removed by filtration, and the filtrate was washed with water (3×100 mL). The organic layer was dried over anhydrous sodium sulfate, and the solvent was removed to give a pale brown viscous liquid (110 g). This material was dissolved in methanol (500 mL) and treated with aqueous 4N NaOH (80 mL). After 4 hours, the reaction mixture was acidified with concentrated HCl, and the solvent was removed under vacuum. The viscous oil was dissolved in dichloromethane and was washed with water (4×100 mL). The organic layer was dried over sodium sulfate, and the solvent was removed to give a bis-5-hydroxypentoxy polyethylene glycol as a pale brown viscous liquid (98 g). The p-nitrophenyl phosphate group was added in a manner analogous to the procedure in Example 61.

The following Examples were prepared using the above procedure.

TABLE 6

Polyethylene glycols having a p-nitrophenyl phosphate lipase inhibiting group tethered by a dialkoxy linker and having a variety of hydrophobic moieties.

| EXAMPLE | PEG MW | HYDROPHOBIC MOIETIES (R) | DIALKOXY ($Z^1$) |
|---|---|---|---|
| 67 | 1500 | n-hexyl | n-pent-1,5-dioxy |
| 68 | 1500 | n-dodecyl | n-pent-1,5-dioxy |
| 69 | 1500 | n-hexadecyl | n-pent-1,5-dioxy |

EXAMPLE 75

Preparation of a BRIJ® polymer having a p-nitrophenyl phosphate lipase inhibiting group and a hexadecyl hydrophobic moiety:

p-Nitrophenyl phosphorodichloridate (75 g, 0.29 mol) in anhydrous dichloromethane (300 mL) was added to a 1 L, three necked, round-bottomed flask with stir bar that had been purged with $N_2$. A solution of hexadecanol (71.03 g, 0.29 mol) and N-methylimidazole (23.35 mL, 0.29 mol) in anhydrous dichloromethane (250 mL) was added dropwise over a period of 2 hours. The reaction mixture was stirred for an additional 1 hour before pouring into a 1 L separatory funnel. N-methylimidazole hydrochloride salts separated at the bottom as an oil and were removed from the funnel. Dichloromethane was removed from the mixture at less than 30° C. under vacuum to give an amber oil which was taken up in hexane (400 mL) and placed in a freezer overnight. The reaction mixture was then thawed and the soluble portion was filtered to remove the crystals of p-nitrophenyl phosphorodichloridate. The solvent was removed from the filtrate via rotary evaporation at less than 35° C. to give n-hexyl p-nitrophenyl phosphorochloridate.

A 500 mL flask with stir bar was purged with $N_2$. The n-hexyl p-nitrophenyl phosphorochloridate (20 g, 0.043 mol) in anhydrous THF (25 mL) was added, followed by slow addition of a solution of BRIJ® 58 (polyoxyethylene (20) cetyl ether; 48.56 g, 0.043 mol) and N-methylimidazole (3.45 mL, 0.043 mol) in anhydrous THF (200 mL). The reaction mixture was stirred at room temperature for 24 hours. The solvent was removed at less than 35° C. by rotary evaporation, and the oily residue was dissolved in methanol (50 mL). A solution of methanol/water (85 mL: 15 mL, 200 mL) was added. The solid bis-n,n-dihexyl p-nitrophenyl phosphate was collected by filtration. The methanol was then stripped off on a rotary evaporator at less than 35° C. Water was removed from the product by lyophilization.

The Examples in Table 7 can be represented by the following structure and were prepared using the above procedure.

TABLE 7

BRIJ ® polymers having a terminal p-nitrophenyl phosphate lipase inhibiting group with a variety of hydrophobic moieties.

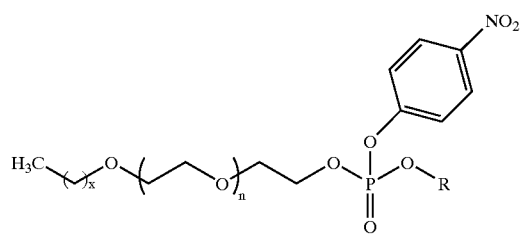

| EXAMPLE | POLYMER | HYDROPHOBIC MOIETY |
|---|---|---|
| 70 | BRIJ ® 98 (n = 19, x = 17) | n-dodecyl |
| 71 | BRIJ ® 98 (n = 19, x = 17) | n-hexadecyl |
| 72 | BRIJ ® 35 (n = 22, x = 11) | n-dodecyl |
| 73 | BRIJ ® 35 (n = 22, x = 11) | n-hexadecyl |
| 74 | BRIJ ® 58 (n = 19, x = 15) | n-dodecyl |
| 75 | BRIJ ® 58 (n = 19, x = 15) | n-hexadecyl |

EXAMPLE 76

Preparation of an IGEPAL® polymer having a terminal p-nitrophenyl phosphate lipase inhibiting group with a n-hexadecyl hydrophobic moieties:

A 500 mL flask with stir bar was purged with $N_2$, and n-hexadecyl p-nitrophenyl phosphorochloridate (20 g, 0.043 mol) in anhydrous THF (25 mL) was added, followed by slow addition of a solution of IGEPAL® 720 (32.41 g, 0.043 mol) and N-methylimidazole (3.45 mL, 0.043 mol) in THF (200 mL). The reaction mixture was stirred at room temperature for 24 hours. The solvent was removed under vacuum at room temperature, and oily product was taken up in methanol (50 mL). A solution of methanol/water (85: 15, 200 mL) was added to product. The bis-n,n-dihexyl p-nitrophenyl phosphate was filtered off, and methanol was then stripped off under vacuum at less than 35° C. Water was removed from the product by lyophilization.

The Examples in Table 8 can be represented by the following structure and were prepared using the above procedure.

TABLE 8

IGEPAL ® polymers having a terminal p-nitrophenyl phosphate lipase inhibiting group with a variety of hydrophobic moieties.

| EXAMPLE | POLYMER | HYDROPHOBIC MOIETY (R) |
| --- | --- | --- |
| 76 | IGEPAL ® 720 (n = 11) | n-dodecyl |
| 77 | IGEPAL ® 720 (n = 11) | n-hexadecyl |
| 78 | IGEPAL ® 890 (n = 39) | n-dodecyl |
| 79 | IGEPAL ® 890 (n = 39) | n-hexadecyl |

EXAMPLE 80

Preparation of [Poly(propylene glycol) block-poly(ethylene glycol) block-poly(propylene glycol)]polymers having a p-nitrophenyl phosphate lipase inhibiting group with a n-hexyl hydrophobic moiety:

A 500 mL flask with stir bar was purged with $N_2$, and n-hexyl p-nitrophenyl phosphorochloridate (20 g, 0.043 mol) in anhydrous THF (25 mL) was added followed by slow addition of a solution of [poly(propylene glycol) block-poly(ethylene glycol) block-poly(propylene glycol)] (average MW=2000, 50 wt. % ethylene glycol; 49.36 g, 0.0215 mol) and N-methylimidazole (3.45 mL, 0.043 mol) in THF (200 mL). The reaction mixture was stirred for 24 hours at room temperature. The solvent was removed under vacuum at room temperature, and the oily residue was taken up in methanol (50 mL). A mixture of 85:15 methanol:water solution (200 mL) was added, and the bis-n,n-dihexyl p-nitrophenyl phosphate precipitate was filtered off. Methanol was stripped off by rotary evaporation at less than 35° C., and water was removed from the product by lyophilization.

The following Examples were prepared using the above procedure.

TABLE 9

Poly(propylene glycol) block-poly(ethylene glycol) block-poly(propylene glycol) polymers (PPG-PEG-PPG) having p-nitrophenyl phosphate lipase inhibiting groups with a variety of hydrophobic moieties.

| EXAMPLE | POLYMER | HYDROPHOBIC MOIETY (R) |
| --- | --- | --- |
| 80 | PPG-PEG-PPG 2000 | hexyl |
| 81 | PPG-PEG-PPG 2000 | dodecyl |
| 82 | PPG-PEG-PPG 2000 | hexadecyl |

EXAMPLE 83

Preparation of a PLURONIC® polymer having phosphochloridate lipase inhibiting groups and a decyl hydrophobic moiety:

After purging with $N_2$, a solution of phophorousoxychloride (30 g, 0.1956 mol) in anhydrous THF (100 mL) was added to a 3 L flask, and the mixture was cooled to 0–5° C. A mixture of freshly distilled triethylamine (27.27 mL, 0.1956 mol) and 1-decanol (30.97 g, 0.1956 mol) in anhydrous THF (300 mL) was added dropwise at a maximum rate of 75 mL/hour, keeping the solution temperature at 5° C. After the addition was complete, a mixture of PLURONIC® (average MW=2900, 142 g, 0.0489 mol) and freshly distilled triethylamine (13.7 mL, 0.0978 mol) in anhydrous THF (300 mL) was added at a maximum rate of 75 mL/hour, keeping the solution temperature at 5° C. After the addition was complete, the reaction was allowed to warm to room temperature and stirred for 24 hours. The triethylammonium hydrochloride salts were removed by filtration. The solvent was removed under vacuum at 30° C., and the resulting oil was washed with hexane (6×250 mL) to remove the unreacted n-decyl phosphorodichloridate. The product, bis-n-decyl phosphorochlorodate PLURONIC®, was dried under high vacuum (0.003 mm Hg) overnight at room temperature.

EXAMPLE 84

Preparation of a PLURONIC® polymer having N-hydroxysuccinimidyl phosphate lipase inhibiting groups and a decyl hydrophobic moiety:

A 125 mL flask with stir bar was purged with $N_2$, and a solution of bis-n-decyl phosphorochlorodate PLURONIC® (prepared as in Example 82; 30 g, 0.0178 mol) was added. N-hydroxysuccinimide (2.05 g, 0.0178 mol) was added as a solid and allowed to dissolve. Freshly distilled triethylamine (2.48 mL, 0.0178 mol) was added, and the reaction mixture was allowed to stir for 0.5 hours. The triethylammonium hydrochloride salt was filtered off, and the THF was removed from the filtrate by rotary evaporation at 30° C. The product was dried under high vacuum (0.003 mm Hg) overnight.

EXAMPLE 85

Preparation of PLURONIC® polymers having pyridoxinyl phosphate lipase inhibiting groups and a decyl hydrophobic moiety:

A 125 mL flask with stir bar was purged with $N_2$, and bis-n-decyl phosphorochlorodate PLURONIC® (prepared as in Example 82; 30 g, 0.0178 mol) in anhydrous dichloromethane (30 mL) was added. Pyridoxine hydrochloride (2.54 g, 0.0178 mol) was added as a solid and allowed to dissolve. Freshly distilled triethylamine (4.96 mL, 0.0356 mol) was added, and the reaction mixture was allowed to stir for 2 hours. The triethylammonium hydrochloride salt was filtered off, and the solvent was removed by a rotary evaporation at less than 35° C. The oil was taken up in THF (50 mL) and refiltered. The solvent was removed by rotary evaporation, and the product was dried under high vacuum (0.003 mm Hg) overnight at room temperature.

Table 10 lists the polymers prepared in Examples 83, 84 and 85.

TABLE 10

PLURONIC ® polymers having a variety of leaving groups.

| EXAMPLE | POLYMER | HYDROPHOBIC MOIETY (R) | LEAVING GROUP (Y—R¹) |
|---|---|---|---|
| 83 | PLU 2900 | decyl | chloride |
| 84 | PLU 2900 | decyl | n-hydroxysuccinyl |
| 85 | PLU 2900 | decyl | pyridoxinyl |

EXAMPLE 86

Preparation of a PLURONIC® polymer having β-lactone lipase inhibiting group (Scheme I):

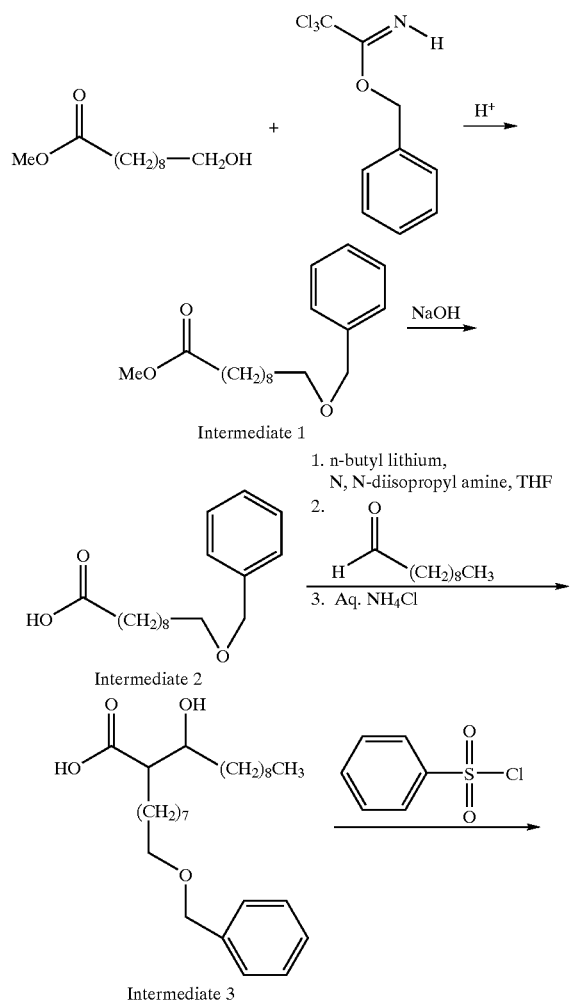

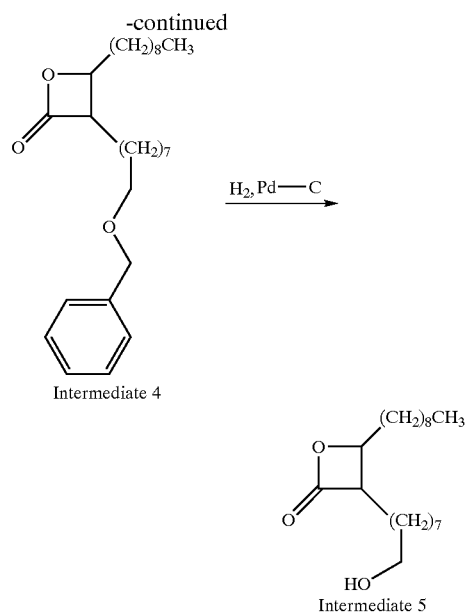

Intermediate 1:

10-Hydroxy methyldecanoate 1 (20 g, 98 mmol), benzyloxy 2,2,2-trichloroacetimidate (30 g, 118 mmol), dichloromethane (50 mL) and cyclohexane (100 mL) were added to a 1 L, round-bottomed flask. The mixture was stirred for 5 minutes at room temperature. Trifloromethane sulfonic acid (1.3 mL) was added to the reaction mixture under nitrogen atmosphere. Within a few minutes the temperature rose from room temperature to 37° C. The reaction was monitored by TLC (hexane:ethyl acetate; 9:1). After 16 hours, the starting material completely disappeared. The solids were separated from the reaction by filtration, and the filtrate was washed with aqueous saturated sodium bicarbonate solution (3×100 mL) followed by water (3×100 mL). The organic phase was collected and dried over anhydrous sodium sulfate. The solvent was removed under vacuum at room temperature. The residue was purified on silica gel column using a gradient of ether/hexane as the mobile phase. The product was eluted from the column in ether-hexane (8:2). The solvent was removed in vacuo to yield 10-benzyloxy methyldecanoate (intermediate 1) as a solid (32 g).

Intermediate 2:

Intermediate 1 (30 g) was saponified in 6N NaOH solution (100 mL) for 12 hours, then acidified with concentrated HCl. The product was extracted with chloroform (5×100 mL). The organic layers were combined and dried over sodium sulfate. The solvent was removed under vacuum to give 10-benzyloxy decanoic acid (intermediate 2) (27 g), which was used directly in the next reaction.

Intermediate 3:

n-Butyl lithium in hexane (1.6 M solution, 68 mL, 108 mmol) was added dropwise to a solution of N,N-diisoproyl amine (15.14 mL, 108 mmol) in THF (50 mL) which was maintained at 0° C. After the completion of addition, the mixture was stirred for an additional 10 minutes at 0° C. The mixture was cooled to −50° C., then a solution of intermediate 2 (15 g, 54 mmol) in 100 mL of THF was added dropwise. After the completion of the addition, the mixture was allowed to warm to room temperature, then stirred for 1 hour. The mixture was cooled to −78° C., and a solution of decyl aldehyde (8.44 g, 54 mmol) in THF (40 mL) was added dropwise. After stirring for 3 hours at −78° C., the mixture was warmed to room temperature, then quenched by addition of saturated ammonium chloride solution (50 mL). The mixture was extracted with diethyl ether (5×50 mL). The organic layers were combined and dried over sodium sulfate, filtered and evaporated to give intermediate 3 (22 g).

Intermediate 4:

Benzenesulfonyl chloride (9.8 g, 56 mmol) was added to a solution of intermediate 3 (12 g, 28 mmol) in pyridine (200 mL) maintained at 0° C. After addition was complete, the mixture was kept in a refrigerator at 4° C. for 24 hours, then poured into crushed ice (2 kg) and stirred at room temperature for 20 minutes. The mixture was extracted with diethyl ether (6×150 mL). The combined organic layers were washed with water, dried over sodium sulfate, filtered and concentrated in vacuo. The product was purified on a silica gel column using hexane:ethyl acetate (9:1) to give intermediate 4 as an oil (9.8 g). IR: $1825^{-1}$ cm.

Intermediate 5:

Intermediate 4 (9.5 g, 22 mmol) was dissolved in methylene chloride, then hydrogenated under 50 psi of hydrogen for 4 hours using 10% Pd/C (1 g) as a catalyst. The solution was filtered, and the solvent was removed under vacuum to give intermediate 5 as an oil (6.9 g).

Intermediate 6:

PLURONIC® (MW=1,900; 570 g; 300 mmol) in THF (500 mL) was added dropwise to a stirred suspension of sodium hydride (15 g) in THF (150 mL). After the addition was complete, the mixture was stirred for an additional 30 minutes at room temperature. A solution of ethyl 4-bromobutyrate (117 g, 600 mmol) was added dropwise, and the mixture was stirred at 60° C. for 16 hours. After cooling to room temperature, the salts were filtered off, and the solvent was removed under vacuum to give light brown viscous material which was suspended in dichloromethane (1 L) and washed with water (3×200 mL). The organic layer was collected and dried over sodium sulfate, filtered, and the solvent was removed under vacuum to give intermediate 6 as a viscous liquid (770 g).

Intermediate 7:

Intermediate 6 was dissolved in a solution of methanol (1 L) and 50% sodium hydroxide solution (100 mL), then stirred for 24 hours at room temperature. The reaction mixture was acidified with concentrated HCl, and the solvent was removed under vacuum. The residue was resuspended in dichloromethane (1 L), then washed with water (4×250 mL). The organic layer was dried over sodium sulfate, filtered, and the solvent was removed under vacuum to give intermediate 7 as a viscous liquid (650 g).

Intermediate 8:

1-(3-Dimethylaminopropyl)-3-ethylcarbodiimide hydrochloride (4.8 g, 25 mmol) was added under nitrogen to a solution of intermediate 7 (20.72 g, 10 mmol) in dichloromethane (100 mL) in a round bottom flask. The mixture was stirred for 10 minutes at room temperature, then N-hydroxy succinimide (2.3 g) was added. The mixture was stirred for 12 hours at room temperature, then transferred to a separatory funnel and was washed with water (3×30 mL). The organic layer was dried over anhydrous sodium sulfate, filtered, and the solvent was removed under vacuum to give 22 g of intermediate 8 which was used directly in the next step.

EXAMPLE 86

Triethylamine (3 mL) was added to a solution of intermediate 8 (22 g, ~10 mmol) and intermediate 5 (6.5 g, 20 mmol) in dichloromethane (150 mL). The mixture was stirred for 4 hours at room temperature, then poured into a separatory funnel and washed with 5% HCl (3×20 mL) and water (3×50 mL). The organic layer was dried over sodium sulfate, filtered, and the solvent was removed under vacuum. Example 86 was obtained as viscous liquid (26 g). This material was used directly in the in vitro and in vivo assay.

EXAMPLE 87

Preparation of a PLURONIC® polymer having a disulfide lipase inhibiting group:

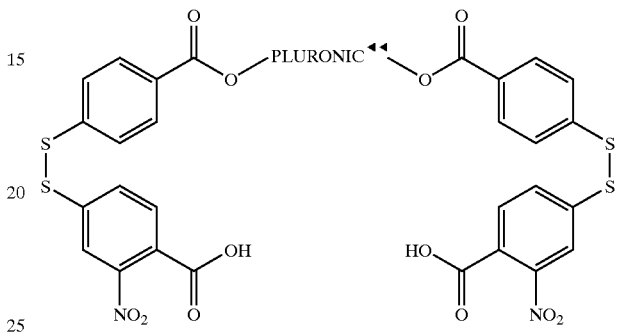

Example 87

Intermediate 9:

1-(3-Dimethylaminopropyl)-3-ethylcarbodiimide (1.1 g, 5 mmol) was added to a solution of 5,5'-dithiobis(2-nitrobenzoic acid) (3.96 g, 10 mmol) in dichloromethane (100 mL). After 10 minutes N-hydroxysuccinimide (0.5 g, 5 mmol) was added, and the reaction was stirred for 6 hours at room temperature. The reaction mixture was poured into a separatory, then washed with water (3×20 mL). The organic layer was dried over anhydrous sodium sulfate, filtered, and the solvent was removed under vacuum to give intermediate 9 which was used directly in the next step.

A solution of PLURONIC® (MW=1,900; 9.5 g; 5 mmol) in dichloromethane (50 mL), followed by triethylamine (0.5 mL) was added to a solution of intermediate 9 in dichloromethane (100 mL). The mixture was stirred for 16 hours at room temperature, then poured into a separatory funnel and washed with water (3×30 mL). The organic layer was dried over anhydrous sodium sulfate, filtered and The solvent was removed under vacuum to give Example 87 as a viscous liquid (12 g).

EXAMPLE 88

Preparation of a PLURONIC® polymer having an anhydride lipase inhibiting group:

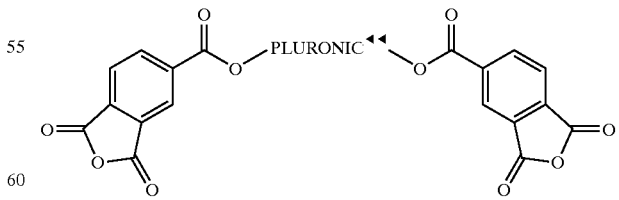

Example 88

Intermediate 10:

1-(3-Dimethylaminopropyl)-3-ethylcarbodiimide (2.2 g, 10 mmol) was added to a solution of 1,2,3-benzene tricarboxylic anhydride (2.1 g, 10 mmol) in dichloromethane (100 mL). The mixture was stirred for 10 minutes, then N-hydroxysuccinimide (1.0 g, 10 mmol) was added, and the reaction was stirred for 6 hours at room temperature. The reaction mixture was poured into a separatory funnel, then washed with water (3×20 mL). The organic layer was dried over anhydrous sodium sulfate, filtered, and the solvent was removed under vacuum to give intermediate 10 which was used directly in the next step.

A solution of PLURONIC® (MW=1,900; 9.5 g; 5 mmol) and triethylamine (0.5 mL) in dichloromethane (50 mL) was added to a solution of intermediate 10 in dichloromethane (100 mL). The mixture was stirred for 16 hours at room temperature, then poured into a separatory funnel and washed with water (3×30 mL). The organic layer was dried over anhydrous sodium sulfate, filtered, and the solvent was removed under vacuum to give Example 88 (11.2 g) as viscous liquid.

In Vitro Assay

Procedure 1: Tributyrin Substrate

Potential inhibitors of pancreatic lipase activity were evaluated using a titration method employing a pH Stat instrument (Radiometer America, Westlake Ohio). Substrate (1 mL tributyrin) was added to 29.0 mL of Tris-HCl buffer (pH 7.0) containing 100 mM NaCl, 5 mM $CaCl_2$, and 4 mM sodium taurodeoxycholate. This solution was stirred for 5 minutes prior to the addition of 210 units of porcine pancreatic lipase (Sigma, 21,000 units/mg) dissolved in the assay buffer. The release of butyric acid by the lipase was monitored over a 10 minute period by titrating the assay system to a constant pH of 7.0 with 0.02 M NaOH. Enzyme activity was expressed as milliequivalents of base added per minute per gram of enzyme. In subsequent assays, varying amounts of inhibitor were solubilized in either tributyrin or buffer, depending on the solubility characteristics of the compound, and added to the assay system at time zero.

Procedure 2: Olive Oil Substrate

Potential inhibitors of pancreatic lipase activity were evaluated using a titration method employing a pH Stat instrument (Radiometer America, Westlake, Ohio). Substrate (15 mL of an olive oil emulsion containing 80 mM olive oil and 2 mM oleic acid, dissolved and sonified in a buffer consisting of 10 mM Tris-HCl pH 8.0, 110 mM NaCl, 10 mM $CaCl_2$, 2 mM lecithin, 1.32 mM cholesterol, 1.92 mM sodium glycocholate, 1.28 mM sodium taurocholate, 2.88 mM sodium glycodeoxycholate, and 1.92 mM sodium taurodeoxycholate) was added to 15 mL of assay buffer (Tris-HCl pH 8.0 containing 110 mM NaCl and 10 mM $CaCl_2$). This solution was stirred for 4 minute prior to the addition of 1050 units of porcine pancreatic lipase (Sigma, 21,000 units/mg) dissolved in assay buffer. The hydrolysis of triglyceride was monitored over a 30 minute period by titrating the assay system to a constant pH of 8.0 with 0.02M NaOH. Enzyme activity was expressed as milliequivalents of base added per minute per gram of enzyme. In subsequent assays, stock solutions of inhibitor were prepared in either ethanol or DMSO, and varying amounts were added to the assay system at time zero.

The assays were conducted as described above using either procedure 1 or 2, and the percent inhibition was derived by comparing the enzyme activities in the presence and absence of inhibitor. Three concentrations of inhibitor were assayed, and the percent inhibition was plotted against the log of the inhibitor concentration in order to determine the concentration at which 50% inhibition occurred ($IC_{50}$). The following compounds were assayed, with the indicated values for $IC_{50}$ presented in Tables 11–17.

TABLE 11

| Example | Polymer | Hydrophobic Moiety | $IC_{50}$ ($\mu$M) with Tributyrin | $IC_{50}$ ($\mu$M) with Olive Oil |
|---|---|---|---|---|
| Polyethylene glycol (PEG) nitrophenyl phosphates: | | | | |
| 10 | PEG 1000 | pentyl phosphate | 400 | *** |
| 11 | PEG 1000 | hexyl phosphate | na | *** |
| 12 | PEG 1000 | octyl phosphate | 538 | *** |
| 5 | PEG 1000 | decyl phosphate | na | *** |
| 6 | PEG 1000 | dodecyl phosphate | 466 | *** |
| 7 | PEG 1000 | tetradecyl phosphate | 1142 | *** |
| 8 | PEG 1000 | hexadecyl phosphate | 67 | 320 |
| 9 | PEG 1000 | octadecyl phosphate | 98 | *** |
| 13 | PEG 1000 | docosyl phosphate | 345 | *** |
| 14 | PEG 1000 | cholesteryl phosphate | 172 | *** |
| 16 | PEG 1500 | pentyl phosphate | na | *** |
| 19 | PEG 1500 | hexadecyl phosphate | 215 | *** |
| 29 | PEG 1500 | octadecyl phosphate | 73 | *** |
| 24 | PEG 1500 | 5-phenyl-1-pentyl phosphate | 24 | 942 |
| 22 | PEG 1500 | farnesyl phosphate | na | *** |
| 23 | PEG 1500 | cholesteryl phosphate | 307 | *** |
| 15 | PEG 3400 | pentyl phosphate | 559 | *** |
| 1 | PEG 8400 | pentyl phosphate | 455 | *** |
| Polypropylene glycol (PPG) nitrophenyl phosphates: | | | | |
| 49 | PPG 1000 | pentyl phosphate | 4000 | *** |
| 53 | PPG 2000 | pentyl phosphate | 52000 | *** |
| PLURONIC ® polymers having nitrophenyl phosphate: | | | | |
| 32 | PLU 1100 | octyl phosphate | 61 | 601 |
| 31 | PLU 1100 | decyl phosphate | 174 | 454 |
| 30 | PLU 1100 | dodecyl phosphate | 55 | 400 |
| 29 | PLU 1100 | tetradecyl phosphate | 133 | 1200 |
| 33 | PLU 1100 | hexyl phosphate | 155 | 353 |
| 39 | PLU 1900 | pentyl phosphate | 3.6 | 9000 |
| 34 | PLU 1900 | octyl phosphate | 3.8 | 379 |
| 35 | PLU 1900 | decyl phosphate | 2.4 | 105 |
| 36 | PLU 1900 | dodecyl phosphate | 2.3 | 183 |
| 37 | PLU 1900 | tetradecyl phosphate | 3.6 | 187 |
| 38 | PLU 1900 | hexadecyl phosphate | 22 | 196 |
| 44 | PLU 2900 | dodecyl phosphate | 1.7 | 286 |
| 43 | PLU 2900 | tetradecyl phosphate | 1.7 | 260 |
| 42 | PLU 2900 | hexadecyl phosphate | 0.9 | 106 |
| 41 | PLU 2900 | octadecyl phosphate | 1.0 | 174 |
| 48 | PLU 4400 | dodecyl phosphate | 8.4 | *** |
| 47 | PLU 4400 | tetradecyl phosphate | 5.0 | *** |
| 46 | PLU 4400 | hexadecyl phosphate | 1.4 | *** |
| 45 | PLU 4400 | octadecyl phosphate | 4.8 | *** |
| 39 | PLU 8400 | pentyl phosphate | 325 | *** |
| 40 | PLU 8400 | hexyl phosphate | 84 | *** |
| Polyethylene glycol (PEG) nitrophenyl phosphonates: | | | | |
| 60 | PEG 1000 | pentyl phosphonate | 836 | na |
| 59 | PEG 1500 | pentyl phosphonate | na | *** |

PLU = PLURONIC ®
PEG = Polyethylene glycol
PPG = Polypropylene glycol
PLU 1,100 (10 wt % PEG monomer, 90 wt % PPG monomer)
PLU 1,900 (50 wt % PEG monomer, 50 wt % PPG monomer)
PLU 2,900 (40 wt % PEG monomer, 60 wt % PPG monomer)
PLU 4,400 (40 wt % PEG monomer, 60 wt % PPG monomer)
PLU 8,400 (80 wt % PEG monomer, 20 wt % PPG monomer)
na= not active;
***not tested

TABLE 12

IC$_{50}$ values of PLURONIC ® polymers having a p-nitrophenyl phosphate lipase inhibiting group and dialkoxy linkers.

| EXAMPLE | PLU MW | HYDROPHOBIC MOIETY (R) | DIALKOXY (Z') | IC$_{50}$ (mM) with Tributyrin | IC$_{50}$ ($\mu$M) with Olive Oil |
|---|---|---|---|---|---|
| 61 | 1900 | n-pentyl | n-pent-1,5-dioxy | 1.8 | na |
| 62 | 1900 | n-decyl | n-pent-1,5-dioxy | 1.1 | 289 |
| 63 | 1900 | n-hexadecyl | n-pent-1,5-dioxy | 1.1 | 278 |
| 66 | 1900 | n-hexadecyl | n-undecyl-1,10-dioxy | 0.8 | 182 |

TABLE 13

IC$_{50}$ values of polyethylene glycol polymers having a p-nitrophenyl phosphate lipase inhibiting group and dialkoxy linkers.

| EXAMPLE | PEG MW | HYDROPHOBIC MOIETY (R) | DIALKOXY (Z') | IC$_{50}$ (mM) with Tributyrin | IC$_{50}$ ($\mu$M) with Olive Oil |
|---|---|---|---|---|---|
| 67 | 1500 | n-hexyl | n-pent-1,5-dioxy | 71 | na |
| 68 | 1500 | n-dodecyl | n-pent-1,5-dioxy | 58 | 371 |
| 69 | 1500 | n-hexadecyl | n-pent-1,5-dioxy | 49 | 184 |

TABLE 14

IC$_{50}$ values for BRIJ ® polymers having a p-nitrophenyl phosphate lipase inhibiting group.

| EXAMPLE | POLYMER | HYDROPHOBIC MOIETY (R) | IC$_{50}$ ($\mu$M) with Tributyrin | IC$_{50}$ ($\mu$M) with Olive Oil |
|---|---|---|---|---|
| 70 | BRIJ ® 98 (n = 19, x = 17) | n-dodecyl | *** | *** |
| 71 | BRIJ ® 98 (n = 19, x = 17) | n-hexadecyl | 250 | 266 |
| 72 | BRIJ ® 35 (n = 22, x = 11) | n-dodecyl | 1800 | 275 |
| 73 | BRIJ ® 35 (n = 22, x = 11) | n-hexadecyl | 1900 | 392 |
| 74 | BRIJ ® 58 (n = 19, x = 15) | n-dodecyl | 1100 | 168 |
| 75 | BRIJ ® 58 (n = 19, x = 15) | n-hexadecyl | 2200 | 428 |

TABLE 15

IC$_{50}$ values for IGEPAL ® polymers having a p-nitrophenyl phosphate lipase inhibiting group.

| EXAMPLE | POLYMER | HYDROPHOBIC MOIETY (R) | IC$_{50}$ ($\mu$M) with Tributyrin | IC$_{50}$ ($\mu$M) with Olive Oil |
|---|---|---|---|---|
| 76 | IGEPAL ® 720 (n = 11) | n-dodecyl | *** | *** |
| 77 | IGEPAL ® 720 (n - 11) | n-hexadecyl | *** | *** |
| 78 | IGEPAL ® 890 (n = 39) | n-dodecyl | 344 | 148 |
| 79 | IGEPAL ® 890 (n = 39) | n-hexadecyl | *** | *** |

TABLE 16

IC$_{50}$ values for PPG-PEG-PPG polymers having
p-nitrophenyl phosphate lipase inhibiting groups.

| EXAMPLE | POLYMER | HYDROPHOBIC MOIETY (R) | IC$_{50}$ ($\mu$M) with Tributyrin | IC$_{50}$ ($\mu$M) with Olive Oil |
|---|---|---|---|---|
| 81 | PPG-PEG-PPG 2000 | n-dodecyl | 2.4 | 283 |
| 82 | PPG-PEG-PPG 2000 | n-hexadecyl | 1.9 | 384 |

TABLE 17

IC$_{50}$ values for PLURONIC® polymers having n-hexadecyl
hydrophobes and a variety of leaving groups.

| EXAMPLE | PLU Mol. wt. | LEAVING GROUP (Z - R$^1$) | IC$_{50}$ ($\mu$M) with tributyrin | IC$_{50}$ ($\mu$M) with Olive Oil |
|---|---|---|---|---|
| 83 | 2900 | chloride | 0.9 | 968 |
| 84 | 2900 | n-hydroxysuccinyl | 0.9 | na |
| 85 | 2900 | pyridoxinyl | 0.09 | 936 |

In Vivo Studies

Examples 8, 35, 36, 41, 42, 48, 62, 63, 67–69, 71–75, 78, 81 and 82 were evaluated for their ability to reduce daily caloric intake by increasing the excretion of fat in the feces, and to decrease body weight gain, relative to the control group, in normal rats over a six day period. Male Sprague-Dawley rats (five to six weeks of age) were individually housed and fed ad libitum a powdered "high fat diet," consisting of standard rodent chow supplemented with 15% fat (consisting of 55% coconut oil and 45% corn oil) by weight. After feeding the animals this diet for five days, the animals were weighed and sorted into the treatment or control groups (6–8 animals per group, each group having equal mean body weights). Animals were treated for six days with the test compounds, which were added to the "high fat diet" at concentrations (w/w) of 0.0% (control), 0.3 or 1.0 percent of the diet.

Food consumption was measured for each animal throughout the study, and was expressed as the total amount of food consumed per animal over the six day treatment period. On day 6, each animal was weighed, and the total body weight gain over the treatment period was calculated.

Rat fecal samples were collected on the final three days of the six days of drug treatment. The samples were freeze dried and ground to a fine powder. One half gram of sample was weighed and transferred to extraction cells. Samples were extracted in an accelerated solvent extractor (ASE 200 Accelerated Solvent Extractor, Dyonex Corporation, Sunnyvale, Calif.) with 95% ethanol, 5% water and 100 mM KOH. The sample was extracted in 17 minutes at 150° C. and 1500 psi. An aliquot of extract was transferred to a test tube containing a molar excess of HCl. The sample was then evaporated and reconstituted in a detergent solution consisting of 2% Triton X-1200, 1% polyoxyethylene lauryl ether and 0.9% NaCl. Fatty acids were then quantitated enzymatically with a colorimetric kit (NEFAC, Wako Chemical GmbH, Neuss, Germany).

Table 18 contains values for fecal fat/consumed fat for both control and test animals (determined enzymatically as described above), and food consumption and body weight gain over 6 days as compared to control animals.

Calculation of Fecal Fat/Consumed Fat:

Fatty acid concentrations from the enzymatic assay are expressed as mmol/mL. The mmol/mL of fatty acid is then multiplied by the number of milliliters of extract generated from 500 mg of sample to give the total mmoles of fatty acid. The value for the total mmoles of fatty acid is converted to total milligrams of fatty acid using the average molecular weight of medium to long chain fatty acid. The value is corrected for any dilutions made during sample work-up. When results are expressed as mgs/gm of feces, the total milligrams of fatty acids is multiplied by 2. When results are expressed as total milligrams of fatty acid excreted in 24 hours, the mgs/gm of feces value is multiplied by fecal weight in grams excreted in 24 hours. When the results are expressed as excreted fat as a percentage of that consumed in 24 hours, the total weight of fat excreted in 24 hours is divided by the weight of fatty acids consumed in over 24 hours and multiplied by 100.

TABLE 18

In vivo results of selected polymers having lipase inhibiting groups.

| Compound Number | Class | Backbone | Hydrophobe | Fecal fat % of consumed | Total food consumption % of control | Total weight change % of control |
|---|---|---|---|---|---|---|
| 8 | phosphate | PEG 1000 | hexadecyl | 2 ± 0.5 | 87 ± 2.8** | 66 ± 9.8** |
| 67 | phosphate | C5 PEG 1500 | hexyl | 3 ± 0.7 | 97 ± 7.8 | 127 ± 64.4 |
| 68 | phosphate | C5 PEG 1500 | dodecyl | 2 ± 0.5 | 99 ± 12.2 | 82 ± 15.4* |
| 69 | phosphate | C5 PEG 1500 | hexadecyl | 3 ± 0.8 | 105 ± 5.5 | 92 ± 8.7 |
| 35 | phosphate | PLU 1900 | decyl | 23 ± 5 | 58 ± 10** | −9 ± 17** |
| 36 | phosphate | PLU 1900 | dodecyl | 12 ± 3 | 62 ± 7** | 16 ± 18** |
| 42 | phosphate | PLU 2900 | hexadecyl | 13 ± 2.5** | 86 ± 8.6** | 75 ± 16.1** |

TABLE 18-continued

In vivo results of selected polymers having lipase inhibiting groups.

| Compound Number | Class | Backbone | Hydrophobe | Fecal fat % of consumed | Total food consumption % of control | Total weight change % of control |
|---|---|---|---|---|---|---|
| 41 | phosphate | PLU 2900 | octadecyl | 15 ± 3.5** | 91 ± 6.2* | 82 ± 6.6** |
| 48 | phosphate | PLU 4400 | dodecyl | 4 ± 1** | 96 ± 7 | 79 ± 8** |
| 81 | phosphate | PPG-PEG-PPG | dodecyl | 2 ± 0 | 92 ± 8 | 78 ± 11** |
| 82 | phosphate | PPG-PEG-PPG | hexadecyl | 2 ± 0 | 114 ± 8 | 129 ± 12** |
| 62 | phosphate | C5 PLU 1900 | decyl | 12 ± 3.2 | 47 ± 2.6 | −24 ± 13.6** |
| 63 | phosphate | C5 PLU 1900 | hexadecyl | 6 ± 1** | 90 ± 5** | 77 ± 13.3** |
| 71 | phosphate | Brij 98 | hexadecyl | 2 ± 1 | 98 ± 6 | 85 ± 11 |
| 72 | phosphate | Brij 35 | dodecyl | 1 ± 0 | 95 ± 5 | 73 ± 13** |
| 73 | phosphate | Brij 35 | hexadecyl | 1 ± 0 | 106 ± 10 | 122 ± 17** |
| 74 | phosphate | Brij 58 | dodecyl | 2 ± 0 | 90 ± 5** | 61 ± 14 |
| 75 | phosphate | Brij 58 | hexadecyl | 1 ± 0 | 104 ± 8 | 100 ± 12 |
| 78 | phosphate | Igepal 890 | dodecyl | 1 ± 0 | 93 ± 5 | 72 ± 13** |
| Control | | | | 2 − 3 | 100 | 100 |

Animals were treated at a dose of 1.0%
*p < 0.05
**p < 0.01

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for treating obesity in a mammal, comprising the step of administering to the mammal an effective amount of a polymer substituted with one or more lipase inhibiting groups, wherein the polymer is substituted with at least one group having the following structure:

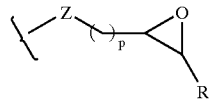

wherein,

R is a hydrogen, hydrophobic moiety, —NR²R³, —CO₂H, —OCOR², —NHCOR², a substituted or unsubstituted aliphatic group or a substituted or unsubstituted aromatic group;

Z is an oxygen, alkylene, sulfur, —SO₃—, —CO₂—, —NR²—, —CONR²—, —PO₄H— or a spacer group;

R² and R³ are, independently, a hydrogen, a substituted or unsubstituted alinhatic group, or a substituted or unsubstituted aromatic group; and p is an integer from zero to about 30.

2. The method of claim 1, wherein the lipase inhibiting groups form a covalent bond with lipase.

3. The method of claim 2, wherein the covalent bond is formed with an amino acid residue at the active site of lipase.

4. The method of claim 2, wherein the covalent bond is formed with an amino acid residue that is not at the active site of lipase.

5. The method of claim 2, wherein lipase is inactivated by non-covalent interaction between the lipase inhibiting group and lipase.

6. The method of claim 5, wherein the lipase inhibiting group is an isostere of a fatty acid.

7. The method of claim 1, wherein the lipase inhibiting group competes with natural triglycerides for lipase hydrolysis.

8. The method of claim 1, wherein the polymer alters the surface of a lipid emulsion.

9. The method of claim 8, wherein the polymer is a fat binding polymer.

* * * * *